US007919444B1

(12) United States Patent
Snyder

(10) Patent No.: US 7,919,444 B1
(45) Date of Patent: Apr. 5, 2011

(54) HOLLOW CELL BATH SOAP

(76) Inventor: Robert George Snyder, Woodstock, GA (US)

( * ) Notice: Subject to any disclaimer, the term of this patent is extended or adjusted under 35 U.S.C. 154(b) by 0 days.

(21) Appl. No.: 12/804,262

(22) Filed: Jul. 19, 2010

(51) Int. Cl.
*A61K 7/50* (2006.01)

(52) U.S. Cl. ......... 510/141; 510/144; 510/152; 401/201

(58) Field of Classification Search ................... 510/141
See application file for complete search history.

(56) References Cited

U.S. PATENT DOCUMENTS 2,195,399 A 4/1940 Eagen
4,308,157 A 12/1981 Di Giovanna
4,438,010 A 3/1984 Lindauer et al.
4,451,386 A 5/1984 Joshi
4,548,572 A 10/1985 Hoffman
4,861,505 A 8/1989 Farman
4,917,589 A 4/1990 Manderson
5,221,506 A * 6/1993 Dulin ............................ 510/120
5,602,088 A 2/1997 Tokosh et al.
5,895,780 A 4/1999 Tokosh et al.
6,036,393 A 3/2000 Youtcheff et al.
7,459,418 B1 12/2008 Ozment

* cited by examiner

*Primary Examiner* — Necholus Ogden, Jr.
(74) *Attorney, Agent, or Firm* — Rodgers & Rodgers

(57) ABSTRACT

A bath soap bar including outer side and end walls interconnected to form a quadrilateral frame. Top and bottom covers are fixed respectively to the top and bottom edges of the frame and multiple internal cells of varying configurations formed by at least two partition walls disposed within the frame.

8 Claims, 4 Drawing Sheets

HOLLOW CELL BATH SOAP

BACKGROUND OF THE INVENTION

This invention relates to soap bars commonly used for human bathing, but could also be used for a variety of cleansing tasks, such as hand cleaning, animal bathing, garment cleaning, parts cleaning, and other such cleaning. In the hotel industry, it is common to provide a fresh bar of bath soap for each new hotel guest. Some luxury hotel brands also commonly provide a fresh bar of bath soap each day, even for a multi-night stay. The resulting disposal of the bath soap used the prior day creates an undesirable waste stream which must be disposed or recycled.

Bath soap, which is commonly provided as a convenience to hotel patrons, creates unnecessary waste when it is disposed after only one or a few uses. Desirable external dimensions of a bar of soap are large enough to be conveniently held in the user's hand while scrubbing or lathering. Desirable structural properties for a bar of soap are to be strong enough to avoid breakage during the bathing process. Because the lathering and cleansing process involves removal of soap material from only the surface of the bar of soap, the interior solid core soap material is not consumed during a single or few uses, thus becomes a waste when it is no longer desirable to use the soap. This is commonly the practice when hotel patrons bath once or twice in a hotel room shower and then check out of the room and depart. The hotel housekeeping personnel discard or recycle the remaining soap bar as waste, prior to the arrival of the next guest, who expects a fresh bar of soap. This is often done to convey a quality appearance and to promote good personal hygiene.

There are various existing designs of bar soap which minimize resulting waste at the end of useful life. However, many focus on subsequent recycling of soap bar remnants, while others rely on a reusable structural core.

U.S. Pat. No. 4,548,572 to Hoffman describes a device which assists bonding of soap remnants to another bar of soap. This design suffers from the requirement that the remnant be reused by the same bather, or it sacrifices the desired quality appearance and good hygiene. U.S. Pat. No. 6,036,393 to Youtcheff suffers from similar shortcomings. U.S. Pat. No. 4,438,010 to Lindauer incorporates an aromatized plastic core, which may or may not be reusable. This design suffers from the requirement to utilize a material core with significantly different physical composition and properties from the soap covering.

U.S. Pat. No. 7,459,418 to Ozment discloses a design for a method of recharging a structural core. The design describes the process of stripping existing soap from the structural core. This design suffers from the requirement to use a material for the structural core which differs significantly from the soap covering which would facilitate the stripping process without damaging the structural core. U.S. Pat. No. 5,221,506 to Dulin describes a solid soap, and suffers from requiring excess raw materials in manufacturing, and residual material for a solid bar.

U.S. Pat. No. 5,895,780 to Tokosh, et al describes a floating soap which specifies a specific ingredient content. This design suffers from the requirement to incorporate a narrow formulation for the soap material.

BRIEF SUMMARY OF THE INVENTION

According to this invention, a bar of bath soap constructed from a hollow soap core with separate but attached top and bottom covers. These covers provide the soap material useful to create lather and cleaning action in the bathing process. The hollow soap core provides structural support for the covers and determines the shape of the overall soap bar. The hollow soap core is constructed with minimum volume of soap which is sufficient to provide structural support for the covers during the bathing process. As the exposed surface of the covers are expended during the bathing process, the covers become thinner. The thickness of the covers result in a minimum post-bath residual thickness which is capable of structurally spanning the cells of the hollow soap core during the bathing process anticipated.

The soap core comprises a variety of two dimensional and three dimensional geometric shapes for the hollow cells with a variety of layout configurations for the number of hollow cells in each row and column with the use of staggered rows and or columns of random placement. Based on the structural properties of the material used for the soap core, the thickness, height and shape of cells and dividing walls can be designed to minimize overall volume of raw material used, while providing desired structural support for the residual covers. With the covers attached to the top and bottom of the cell walls, diaphragm structural support by the covers can provide lateral stability for an otherwise thin and unstable hollow soap core.

Another aspect of the present design is that different soap formulations may be used for the top cover, hollow core, and the bottom cover. These different formulations result in different physical properties for each element, such as structural strength, lathering, solubility, abrasion, color, texture, fragrance, moisturizing, medication, skin-health ingredients and other desirable aspects. More than one separate formulation may be used on each cover, with the resulting overall structure having two or more separate adjoining cover pieces.

The hollow soap is produced by a variety of processes, such as extrusion, casting, machining. The covers are produced and attached by a variety of processes, such as laminating, casting, spraying, dipping, or other process well known in the art. One process of producing the hollow cell bath soap of the present design is by extruding a thin-walled hollow soap core. Extrusion facilitates soap core designs with thinner walls than is possible with other processes.

DETAILED DESCRIPTION OF THE INVENTION

The soap bar of the present invention is constructed from a top cover, a hollow cell soap core and a bottom cover. Two or more adjoining elements may be used in construction each cover. The top cover and bottom covers may also be wrapped around to cover the side walls and end walls of the soap bar. The bar of soap is assembled by attaching the top cover to the top edge of the hollow soap core and by attaching the bottom cover to the bottom edge of the hollow soap core. The interconnection is completed by a variety of methods such as lamination, casting, dipping, spraying or pressure.

Figure 1:
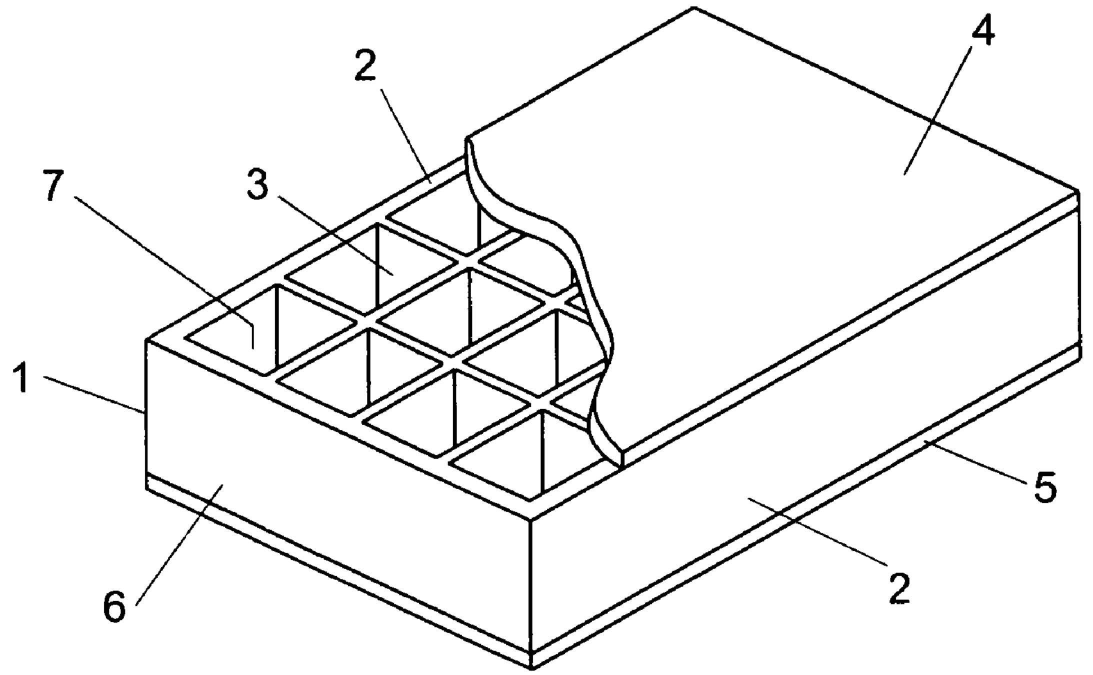
FIG. 1 is a top perspective of the present invention. A portion of the top cover has been removed for clarity to reveal the hollow cell soap core.

In FIG. 1, hollow core 1 is shown attached to bottom cover 5 and top cover 4. A portion of top cover 4 has been removed in the foreground for purpose of clarity. Hollow core 1 includes opposed parallel side walls 2 and opposed parallel end walls 6 which are interconnected to form a frame. Top cover 4 is attached to the top edge of every partition wall 3 and the top edge of every side wall 2 and end wall 6. This creates a structural diaphragm system to provide lateral stability for the thin partition wall 3 elements. Hollow core 1 is constructed with the hollow cells in a variety of two-dimensional or three-dimension shapes. In FIG. 1, rectangular-shaped hollow cells are shown. The interior of the hollow core 1 shown includes a series of partition walls 3 which, along with side wall 2 and end wall 6, create the rectangular hollow cells 7. The thickness of side walls 2 and end walls 6 may be the same, greater than, or less than the thickness of partition walls 3. The various partition walls 3 may vary in thickness. Side walls 2 and end walls 6 having thicker dimensions than the partition wall 3 may be preferred for structural strength in the completed soap bar.

Figure 2:
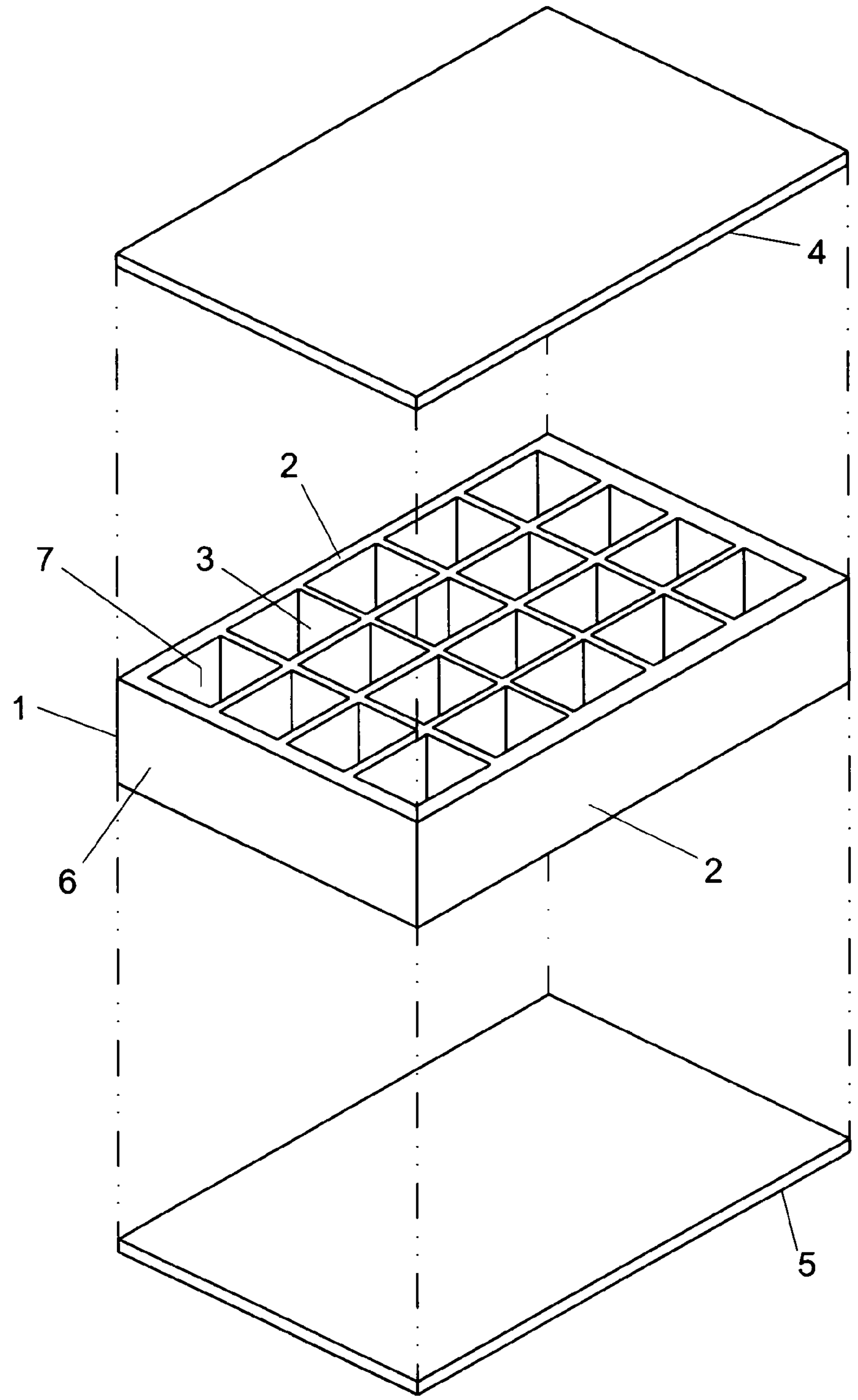
FIG. 2 is an exploded top perspective of the present invention. The top cover, hollow core and bottom core are shown prior to joining them together.

In FIG. 2, hollow core 1, top cover 4, and bottom cover 5 are shown prior to assembly. Single elements are shown for the top cover 4 and bottom cover 5.

Figure 3:
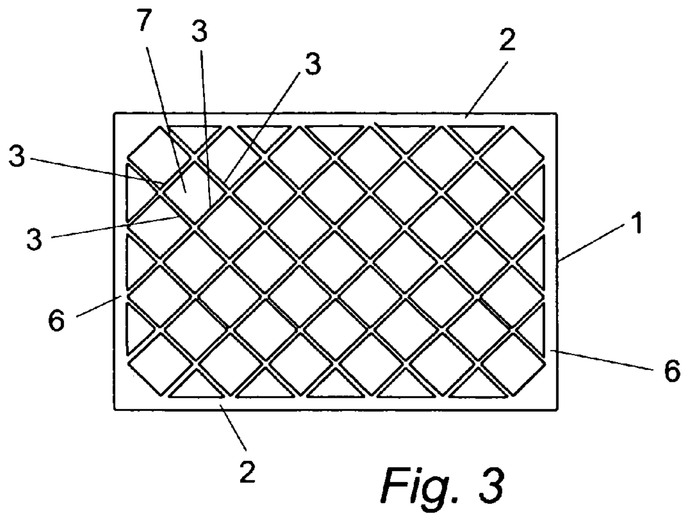
FIG. 3 is a plan view of one possible configuration for the layout of the cells in the hollow soap core in the present invention.

In FIG. 3, the hollow core 1 is shown prior to connecting to the other cover elements. This figure shows a hollow core 1 with a combination of diamond and triangle shaped hollow cells 7. Hollow core 1 is bounded by two side walls 2, and two end walls 6. Aligned, staggered, off-set or irregular rows or random placed arrangement of hollow cells 7 may be used. Other geometric two dimensional shapes, such as rectangular, round, oval, or star may be used. Hollow cells 7 with varying cross-section geometries may also be used.

Figure 4:
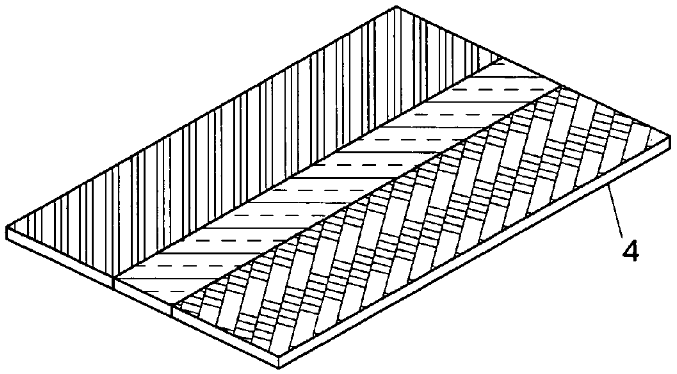
FIG. 4 is a top perspective of the present invention illustrating an embellishment which incorporates three top cover elements.

In FIG. 4, an example of top cover 4 comprised of three different structured elements is shown. One or more elements may be used for top cover 4 and bottom cover 5 (not shown). The three elements shown may vary in physical appearance or physical properties.

Figure 5:
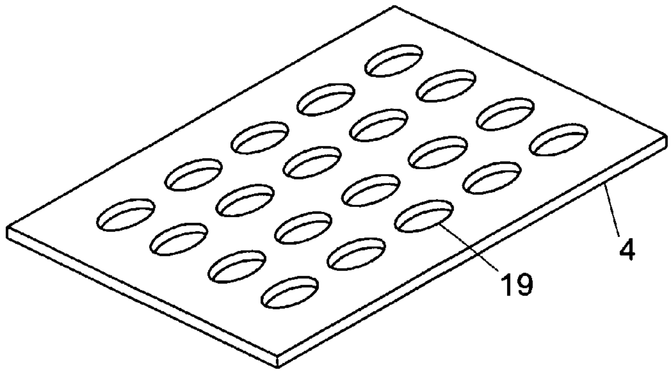
FIG. 5 is a top perspective of the present invention illustrating an embellishment which incorporates a perforated cover.

In FIG. 5, an example of a top cover 4 with reduced volume of material is shown. One or more perforation 19 openings may be used to further reduce the amount of raw material used for the complete soap bar and subsequent post-bathing residual waste. Aligned, staggered, off-set or irregular rows or random placed arrangement of perforation 19 openings may be used. Geometric two dimensional shapes, such as rectangular, round, oval, star, logo or other shapes may be used for the perforation 19 openings.

Figure 6:
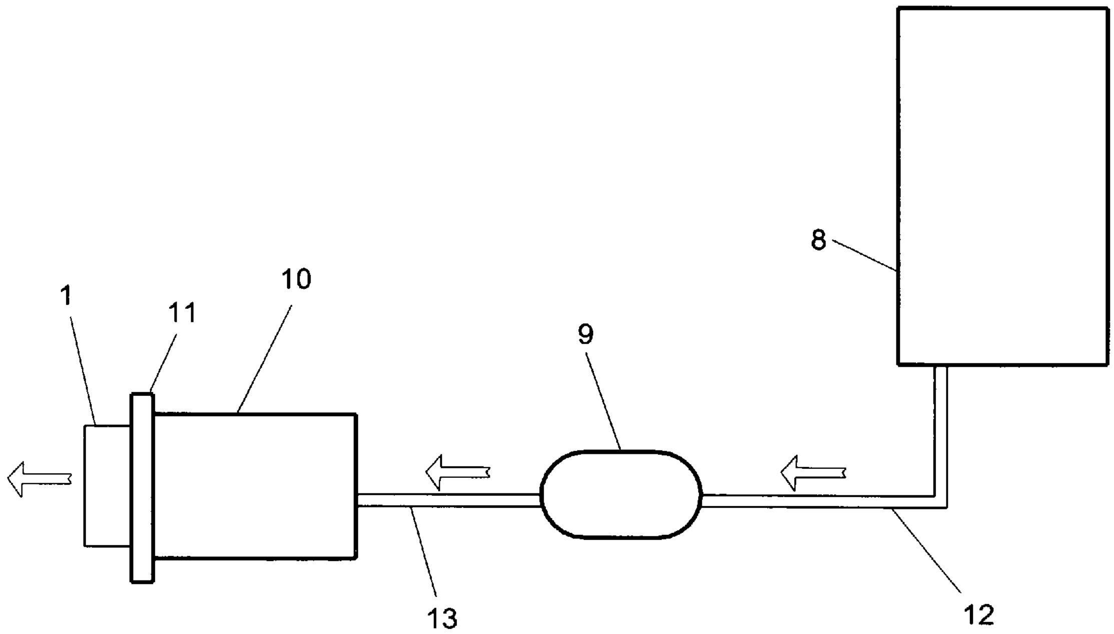
FIG. 6 is a schematic layout of an extrusion process that may be used in producing hollow cell bath soap of the present invention.

In FIG. 6, an extrusion process is shown. Vat 8 contains a supply of raw soap material, which may be liquid or semisolid in state, and may also be heated. Conduit 12 connects vat 8 to pump 9. Pump 9 provides the mechanical force necessary to move the raw soap material from vat 8 through conduit 12, through conduit 13 and finally to and through mold 10. Mold 10 is constructed with a series of casting elements which create the hollow cell 7 elements (not shown) of the hollow core 1. The casting elements may be constructed with capability for selectively varying their cross-sectional shape as the hollow core 1 is progressing through the mold 10. By varying the shape or size of mold 10 as the extrusion process moves from start to finish, hollow cells 7 with varying three-dimensional characteristics can be produced. External or internal heat or chilled sources may be applied to vat 8, conduit 12, pump 9, conduit 13 and mold 10 to facilitate pumping the raw material through the process and to create a stable hollow core 1 upon exiting the mold 10. Shear 11 is used to sever hollow core 1 from the molded soap raw material still in the mold 10. Shear 11 may be constructed by a variety of designs well known in the art, such as a knife, wire, water jet, or air jet.

Figure 7:
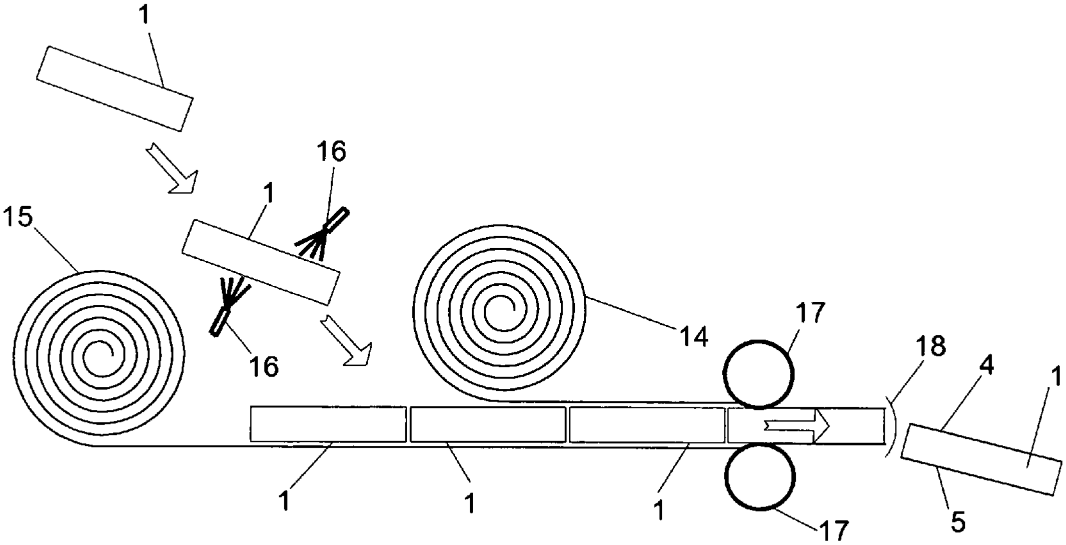
FIG. 7 is a side elevation view of a laminating process which may be used in producing hollow cell bath soap of the present invention.

In FIG. 7, several hollow cores 1 are introduced into the laminating machine. The top and bottom edge surfaces of the hollow core 1 elements are sprayed with liquid adhesive such as liquid soap by nozzle 16, as they enter the laminating process. Nozzle 16 may also be a source of heat or flame to facilitate the laminating action. Top raw material 14 and bottom raw material 15 provide feed stock for top cover 4 and bottom cover 5. The top raw material 14 and bottom raw material 15 are pressed against the hollow core 1 by roller 17 elements. Trimmer 18 severs the raw material stock to release the completed hollow soap bar.

The invention claimed is:

1. Bath soap bar comprising a hollow core, said hollow core including a pair of parallel spaced side walls and a pair of parallel spaced end walls interconnected to said side walls to form a quadrilateral planar frame, said frame having upper and lower edges, a top cover secured to said upper edge, a bottom cover secured to said lower edge, and said hollow core comprising multiple hollow cell elements.

2. A bath soap bar according to claim 1 wherein said hollow cell element comprises at least two perpendicular partition walls.

3. A bath soap bar according to claim 1 wherein said hollow cell elements are of varying cross-sectional configurations.

4. A bath soap bar according to claim 1 wherein said hollow cell element comprises at least one perpendicular partition wall and at least one of said end or side walls.

5. A bath soap bar according to claim 1 wherein said soap bar is formed by means of an extrusion process.

6. A bath soap bar according to claim 2 wherein the thickness of said partition walls is different than the thickness of said end and side walls.

7. A bath soap bar according to claim 1 wherein at least one opening is formed in one of said covers.

8. A soap bar according to claim 7 wherein said opening is formed in said top cover.

* * * * *